United States Patent [19]

Nishino et al.

[11] Patent Number: 5,008,295
[45] Date of Patent: Apr. 16, 1991

[54] METHOD INHIBITING THE GROWTH OF CANCER CELLS

[75] Inventors: Hoyoku Nishino, Hirakata; Ryozo Iwasaki, Tokyo; Akio Okabe, Tokyo; Yuki Yogo, Tokyo, all of Japan

[73] Assignee: Lion Corporation, Tokyo, Japan

[21] Appl. No.: 225,020

[22] Filed: Jul. 28, 1988

[30] Foreign Application Priority Data

Jul. 30, 1987 [JP] Japan ................................. 62-191301

[51] Int. Cl.$^5$ ............................................ A61K 31/015
[52] U.S. Cl. .................................................. 514/766
[58] Field of Search ........................................ 514/766

[56] References Cited

PUBLICATIONS

H. Nishino et al, J. Kyoto Pref. Univ. Mde., vol. 97, No. 9, pp. 1097–1102, (Sep. 1988).
The Merck Index, 10th Ed., 1983, pp. 258–259.
The Lancet, pp. 325–326, Aug. 11, 1984.
Kummet et al, Seminars in Oncology, vol. 10, No. 3, pp. 281–289, Sep. 1983.
Murakoshi et al, J. National Cancer Inst., vol. 81, No. 21, pp. 1649–1652, Nov. 1989.
Schwartz et al, Biochemical and Biophysical Research Communications, vol. 136, No. 3, pp. 1130–1135 (1986).
Micheline M. Matthews-Roth, Oncology 39: 33–37 (1982).
Dyer, An Index of Tumor Chemotherapy, WIH, Mar. 1949, pp. 10, 11 and 149.
Chemical Abstracts 103:220824g and 220825h (1985).

*Primary Examiner*—Jerome D. Goldberg
*Attorney, Agent, or Firm*—Birch, Stewart, Kolasch & Birch

[57] ABSTRACT

A method of inhibiting the growth of cancers susceptible to treatment with α-carotene, which comprises: administering an effective cancer cell growth inhibiting amount of α-carotene to a manmal having said cancer cells.

9 Claims, 3 Drawing Sheets

METHOD INHIBITING THE GROWTH OF CANCER CELLS

BACKGROUND OF THE INVENTION

1. Field of the Invention

The present invention relates to a method of inhibiting the growth of cancer cells which are susceptible to treatment with antitumor drugs.

2. Description of the Prior Art

These days, cancer is generally treated by surgery, radiotherapy, chemotherapy (treatment with drugs), etc.

So far, chemotherapy with drugs acting directly on tumor cells to kill them has been widespread, and thus there have been many proposals as to such drugs. These drugs, however, act not only on tumor cells to kill them but also on normal cells, and thus can not produce their high therapeutic effects without being accompanied by extremely severe side effects.

Under the circumstances, attention has been drawn to drugs for enhancing immunological competence of normal cells to indirectly inhibit growth of tumor cells. Examples of such drugs are Krestin and interferon. The direct effects of such drugs on tumor cells is small but advantageous because of the low side effects.

Recently, from the viewpoint of decarcinogenesis of tumor cells (carcinogenesis is not irreversible but reversible, that is, tumor cells can be caused to approach or revert to normal cells), attention has also focused on the use of drugs capable of performing differentiation-inducing action to transform tumor cells into normal cells. These drugs have direct action on tumor cells with less side effects, and thus can be expected as promising antitumor agents which might have high therapeutic effects.

Hitherto agents have been proposed having differentiation-inductive activity, such as prostaglandin $E_1$ which causes an increase of c-AMP. However, prostaglandin $E_1$ is so unstable in the human body that it must be drip-infused directly to an affected site for treatment of cancer and must be used in combination with other drugs. Under the circumstances, substances having good differentiation-inductive activity and which can be effectively used as an antitumor drug with stability and low toxicity are desired.

SUMMARY OF THE INVENTION

The inventors have found that α-carotene has powerful growth-inhibitory effects on cancer cells susceptible to treatment therewith.

According to the present invention, there is provided a method of inhibiting growth of cancer cells which are susceptible to treatment with α-carotene, which consist essentially of administering an effective amount of α-carotene to a mammal having such cancer cells. It is contemplated that the method of the present invention will be useful in the treatment of cancer in various types of warm blooded mammals including lower animals such as rats or mice as well as humans.

β-carotene is known to have antitumor activity on the lymphocytic system as disclosed in the paper, Oncology 39, 33–37 (1982). The antitumor effects of β-carotene are also disclosed by Schwartz et al, "BIOCHEMICAL AND BIOPYSICAL RESEACH COMMUNICATIONS", p. 1130–1135 (1986). No report telling that α-carotene has similar activity has been published. In contrast to β-carotene showing little inhibitory effect on the growth of cancer cells, α-carotene proved to have excellent characteristics in inhibiting the growth of cancer cells, susceptible to treatment therewith, as is apparent from the later-described Examples. The inventors have also presented new evidence that α-carotene has superior cancer cell growth inhibiting activity in cancers susceptible to treatment therewith, and thus can be used with good chemotherapeutic effects.

DETAILED DESCRIPTION OF THE INVENTION

Figure 1:
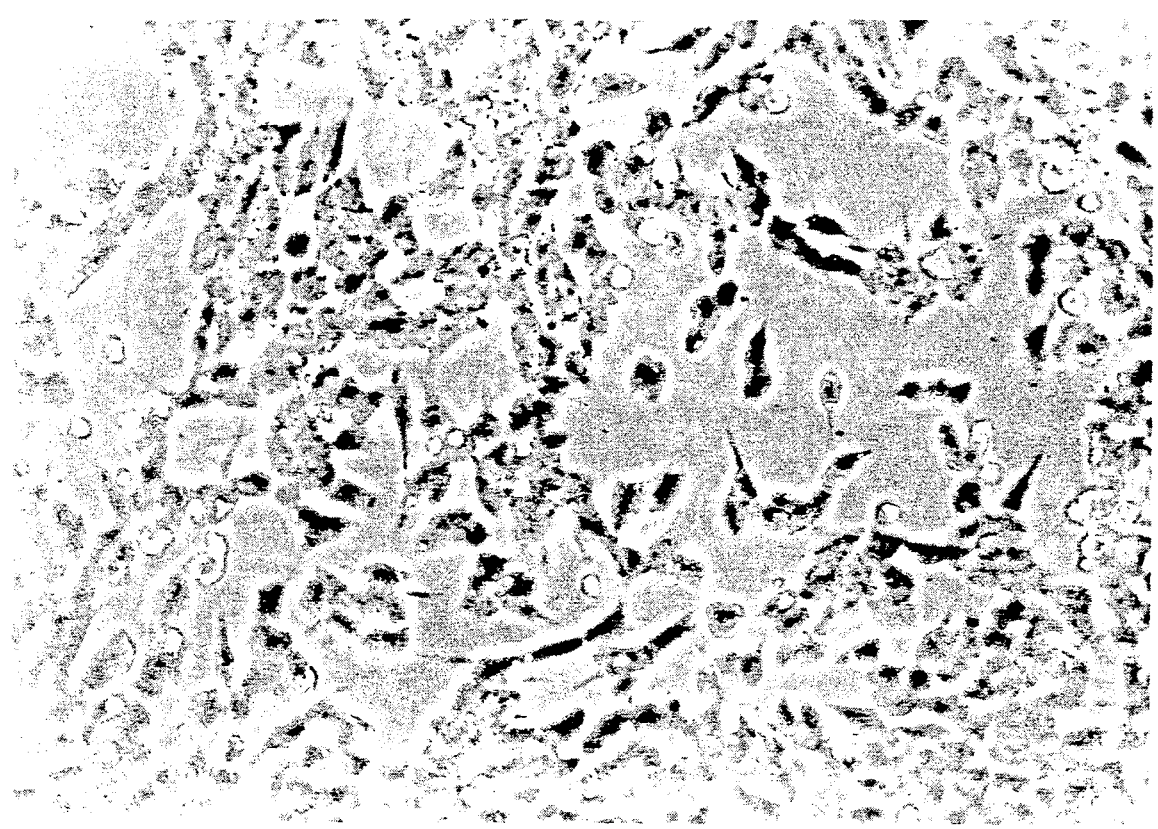
FIG. 1 is a microscopic photograph showing the morphological change of GOTO cells in a control cultivation containing no α-carotene.

Cancer cell growth inhibiting drugs according to the invention contain α-carotene as an effective component for the treatment of cancer cells susceptible to treatment therewith.

α-Carotene suitable for use in the present invention includes natural and synthetic α-carotenes. Natural α-carotene occurs usually as mixtures with other carotenes, such as β-carotene and γ-carotene. The drugs according to the invention may contain such a carotene mixture. An especially suitable natural carotene for use in obtaining purified α-carotene is a preparation (palm carotene) extracted, concentrated and purified from palm oil, which is a red opaque paste-like mixture of carotenes, and in which about 25 to about 40% by weight of α-carotene, about 50 to about 70% by weight of β-carotene and less than 10% by weight of other components including carotenoids are mixed. The preparation (palm carotene) has a better solubility in oils and good absorbability in the human body when administered. The producing process of palm carotene is disclosed in UK Patent No. 2160874.

Purified and isolated α-carotene from various carotene mixtures may be used in the invention. It is noteworthy that the use of isolated α-carotene as an effective component according to the invention produces as powerful an inhibitory effect on the growth of cancer cells susceptible to treatment therewith, as compared with carotene mixture containing a corresponding amount of α-carotene.

The purified and isolated α-carotene may be prepared according to conventional methods.

The cancer cell growth inhibiting compositions in accordance with the invention of which the effective component is α-carotene, as above-stated, whether α-carotene only or carotene mixtures containing α-carotene, can be administered alone or in combination with other medicines and via various routes. For instance, α-carotene may be administered by intravenous, subcutaneous or intramuscular injection, topically or orally or by a suppository inserted into the rectum. The dose can be set in a wide range (for example, 15 μg to 3 g daily 1 kg body weight or 1 mg to 10 g daily per adult) in accordance with administration route, the number of administrations, and severity of symptoms.

Pharmaceutical compositions according to the invention can be prepared in various combinations with a suitable amount of a sterile non-toxic carrier and an effective amount of α-carotene by any known method. Preparations are made for oral administration in the form of soft and hard capsules, tablets, granules, grains, powder, one permitting sustained release of the effective component, liquid, suspention, etc. and for parenteral administration, in the forms of injections, drops and suppositories, etc. Suitable examples of non-toxic carriers for use in the invention are as follows: surface active agents such as sucrose fatty acid ester, fatty acid monoglyceride, propyleneglycol fatty acid ester, sorbitan fatty acid ester, lecithin, etc.; binders such as gum arabic, gelatin, sorbit, tragacanth gum, polyvinyl pyrrolidone, etc.; vehicles such as sucrose, lactose, starch, crystalline cellulose, manitol, light silicic acid anhydride, magnesium aluminate, magnesium metasilicate aluminate, synthetic aluminum silicate, calcium carbonate, sodium bicarbonate, calcium hydrogenphosphate, calcium carboxymethyl cellulose, etc.; lubricants such as magnesium stearate, talc, hardened oil, etc.; seasoning or flavoring agents such as sodium chloride, saccharin, orange oil, licorice extract, citric acid, glucose, menthol, eucalyptus oil, malic oil, etc.; suspending or wetting agents such as coconut oil, olive oil, sesame oil, peanut oil, soybean oil, not so long chain fatty acid glycerides, safflower oil, soybean phospholipid, etc.; carbohydrate derivatives such as celluloses (acetate phthalate (CAP), etc.), saccharides, etc.; acrylic copolymers such as methyl acrylatemethacrylic acid copolymer, methyl methacrylatemethacrylic acid copolymer, etc.; polyvinyl derivatives such as dibasic acid monoesters, etc.; film forming agents, coating aids, etc. Any conventional methods may be used for obtaining these preparations. Mucous membranes-used preparations and injections may be prepared by conventional techniques. For suspension in or emulsification with distilled water, if applied, can be used soybean oil, peanut oil, not so long chain fatty acid triglyceride, etc. as suspending agents, and sucrose fatty acid ester, fatty acid monoglycerides, propylene glycol fatty acid ester, sorbitan fatty acid ester, lecithin, etc.

α-Carotene which is the effective component of drugs for inhibiting cancer cell growth according to the invention has a powerful inhibitory effect on the growth of cancer cells susceptible to treatment therewith cancer cell growth inhibiting. The cancer cell growth inhibiting pharmaceutical compositions in which the effective component is α-carotene are so low in toxicity that no toxicity appears in doses of 3.5 g of α-carotene per kg of body weight in mice as α-carotene. It is stable in the body, which permits large dose administration of it alone without needing concomitant treatment with other drugs, and thus is administered effectively to treat cancer cells of not only ectodermal origin but also cancer cells of endodermal origin which are susceptible to treatment therewith, such as brain tumor cells, leukemia, gastric, pancreatic, hepatic and cervic cancer cells, etc., especially neuroblastoma.

DESCRIPTION OF THE PREFERRED EMBODIMENTS

Embodiments of the invention, in particular demonstrating the effects of the effective component, will be described in detail.

EXAMPLE 1

Growth-Inhibitory Effect on Human Neuroblastoma Tumor Cells

Human Neuroblastoma cells (GOTO cells) were spread over a Petri dish (inner diameter 35 mm) to make a population of $4 \times 10^4$ cells/ml culture medium/dish and incubated for 2 days.

On the other hand, a 1% emulsion of palm carotene extracted, concentrated and purified from palm oil (2.15 parts by volume) was mixed with 95% ethanol (7.85 parts by volume) and sterilized.

To the tumor cell-cultured dish, 10 μl of the sterilized palm carotene (the last concentration: 20 μM containing α-carotene of 6 μM and β-carotene of 14 μM.) was added, and incubated for 5 days. Control cultivation was made in the same procedure except the use of a carotene-free emulsion.

After completion of cultivation, the number of tumor cells was counted in each dish, and the ratio in number to control was calculated in duplicate to obtain the growth-inhibitory effect of palm carotene on the tumor cell.

Besides the above, the growth-inhibitory effects of α-carotene (2 μM added) and β-carotene (2 μM added) on the tumor cancer cells were also investigated in the same way as in palm carotene.

Differentiation-Inductive Effect

Observation was conducted of α-carotene (2 μM added) culture and control culture to note morphological changes in the GOTO cells, and the effect of α-carotene was expressed as the differentiated cell rate (referred to as differentiation index, hereinafter) represented by the following equation:

$$\text{Differentiated cell rate (\%)} = \frac{\text{No. of Differentiated cells}}{500 \text{ selected-cells}} \times 100$$

where the term "differentiated cells" means those out of 500 selected-cells (cells found in a dish selected as having a gaugeable projection) having a projection at least twice as long as the major diameter of the cell.

The obtained results are given in Tables 1 and 2.

TABLE 1

| | Growth-inhibitory effect on tumor cells | |
|---|---|---|
| | No. of tumor cells ($10^{-5}$ Cells/dish) | Rate of tumor cell No. to control (%) |
| Control | 6.73 | — |
| Palm carotene (20 μM) | 3.01 | 44.7 |

TABLE 2

| | Growth-inhibitory effect on tumor cells | | Differentiation inductive effect (Differentiation index (%)) |
|---|---|---|---|
| | No. of tumor cells ($10^{-5}$ cells/dish) | Rate tumor cell No. to control (%) | |
| Control | 9.90 | — | 4.0 |
| α-carotene (2 μM) | 3.49 | 35.3 | 74.0 |
| β-carotene (2 μM) | 9.58 | 96.8 | — |

The results in Table 1 show that palm carotene containing α-carotene and β-carotene has growth-inhibitory effect on the human neuroblastoma tumor cells (GOTO cells).

The results in Table 2 demonstrates that α-carotene exhibits powerful growth-inhibitory effect on the tumor cancer cell compared with β-carotene having slight similar effect, and it therefore has been proven that α-carotene is involved in the effect of palm carotene.

The data in Table 2 also shows, that tumor cancer cells cultivated in the presence of α-carotene became differentiated with the development of projections proper to neuroblasts (morphological differentiation) into normal cells by the action of α-carotene (2 μM).

Figure 2:
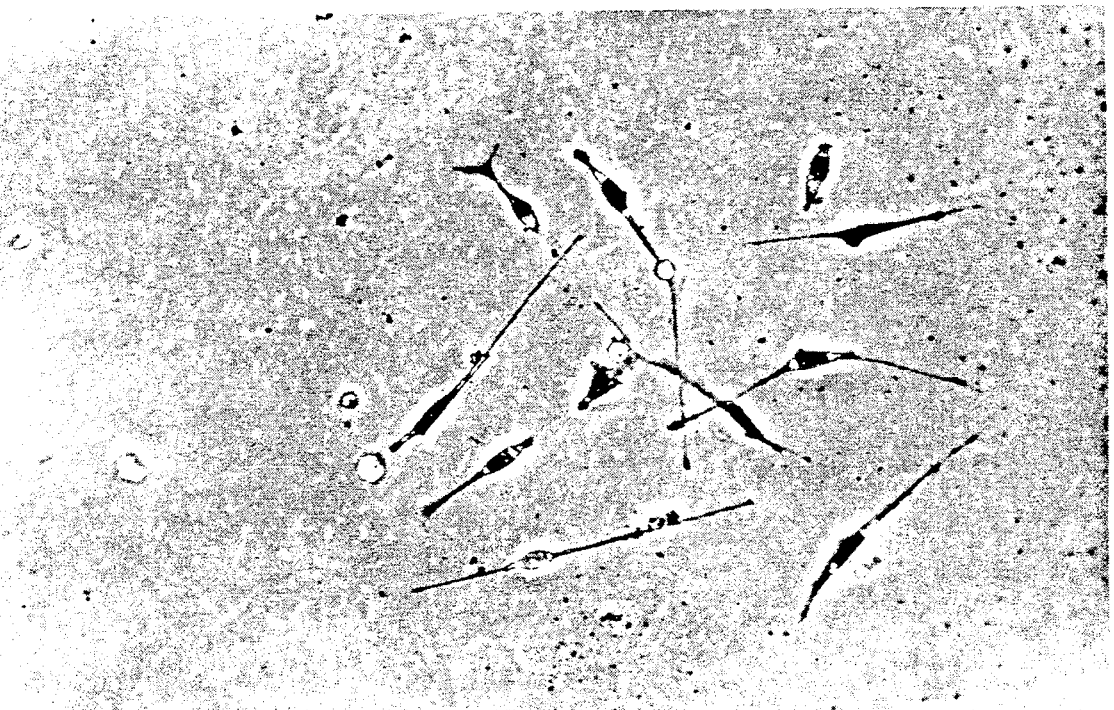
FIG. 2 is a microscopic photograph showing the morphological change of GOTO cells treated with α-carotene after 5 days of cultivation.

FIGS. 1 and 2 are microscopic photographs (magnification is 400) of control cells and cells treated with α-carotene (2 μM) after 5 days of cultivation, respectively, from which the morphological change of GOTO cells (neuroblasts) caused by α-carotene, that is, the effect of α-carotene to reverse the tumor cancer cell into normal cells, can be clearly seen.

EXAMPLE 2

With human tumor cancer cell shown in Table 3 and 20 μM of α-carotene and β-carotene, cultivation was conducted in the same way as in Example 1, and then the numbers of cells in the cultures were counted. The rates in the numbers of those cultures to control culture with carotene-free culture medium were calculated to evaluate the growth-inhibitory effects of the carotenes on the tumor cancer cells, and the results are listed in Table 3.

TABLE 3

Growth-inhibitory effects on different tumor cells

| Tumor cell | α-carotene 20 μM (%) | β-carotene 20 μM (%) |
|---|---|---|
| Pancreatic cancer (PANC-1) | 3.8 | 40.5 |
| Gastric cancer (HGC-27) | 1.3 | 10.9 |
| Hepatic cancer (HLF) | 22.5 | 77.5 |
| Glioblastoma (A-127) | 2.3 | 42.0 |

The results in Table 3 show that α-carotene has beneficial effects on various tumor cancer cells to inhibit effectively their growth as compared with β-carotene.

EXAMPLE 3

With human tumor cancer cells shown in Table 4 and 10 μM of α-carotene, cultivation was conducted in the same way as in Example 1, and then the numbers of cells in the cultures were counted. The rates in the numbers of those cultures to control culture with carotene-free culture medium were calculated to evaluate the growth-inhibitory effects of the carotene on tumor cancer cells, and the results are listed in Table 4.

TABLE 4

| Tumor Cell | Rate of Tumor Cell number to control (%) |
|---|---|
| Neuroblastoma (GOTO) | 1.4 |
| Glioblastoma (A-127) | 39.6 |
| Leukemia (HL-60) | 33.3 |
| Gastric cancer (HGC-27) | 23.5 |
| Pancreatic cancer (PANC-I) | 48.1 |
| Hepatic cancer (HLF) | 55.0 |
| Cervic cancer (Hela) | 77.9 |

The results in Table 4 also show α-carotene has growth inhibiting effect on various tumor cancer cells regardless of their embryonal origin, i.e. ectoderm and endoderm. Both solid tumor cancer cells and leukemia cancer cells are sensitive to the treatment with α-carotene.

EXAMPLE 4

30 mice were divided into two groups each consisting of 15 members. The fur on the back of each mice was shaved off over a relatively large area. Dimethyl benzoanthracene (DMBA) acetone solution was applied to the shaved area of each mice (100 μg DMBA/mouse).

One week after, 12-O-tetradecanol phorbol 13-acetate (TPA) acetone solution was applied to the DMBA-applied area of each mice of one group twice a week (0.5 μg TPA/mouse/application) as a control and, on the other hand, TPA acetone solution containing palm carotene (30% of α-carotene, 65% of β-carotene and 5% of other carotenoids) was applied to the DMBA applied area of each mice of another group twice a week (162 n mol palm carotene/mouse/application, and 0.5 μg TPA/mouse/application) and the number of tumor-bearing mice in each group was examined.

Figure 3:
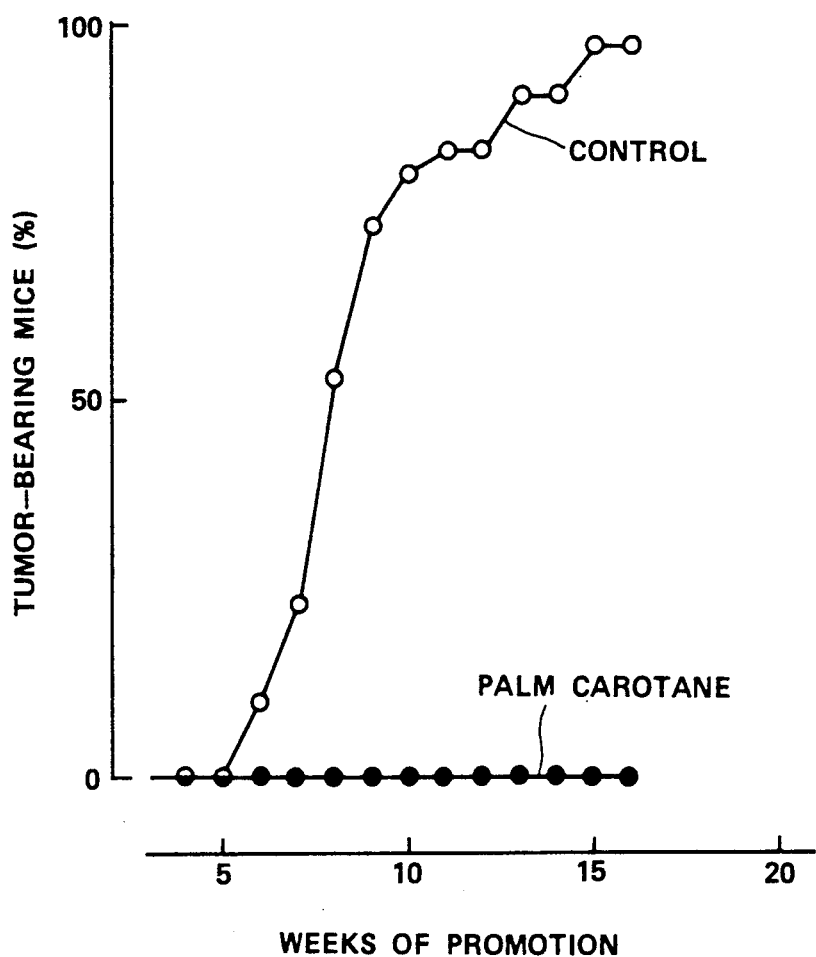
FIG. 3 is a graph showing an effect of palm carotene on the tumor cancer cell promoting effect of TPA in DMBA initiated mice.

The results are shown in FIG. 3.

From the results, palm carotene containing α-carotene had an excellent effect in inhibiting the growth of cancer cells susceptible to treatment therewith in the treated mice.

Preparations according to the invention are prepared, for example, by the following procedures:

PROCEDURE 1 (CAPSULE)

Palm carotene (100 g) is suspended in wheat embryo bud oil (1 kg), and then filled in 1000 gelatin capsules. One to ten capsules are administered daily.

PROCEDURE 2 (INJECTION)

Palm carotene (100 g), stearic acid monoglyceride (100 g), peanut oil (200 g), sucroseglycerinstearyl ester (50 g), ascorbic acid stearate (20 g), and distilled water for injection (9530 g) are mixed to form an injectable solution. The preparation is filled in ampoules at a rate of 10 ml each ampoule.

PROCEDURE 3 (EXTERNAL OINTMENT)

Polyethyleneglycol 4000 (150 g), polyethyleneglycol 400 (150 g) and α-carotene (1 g). The preparation is mixed with warming.

PROCEDURE 4 (SUPPOSITORY)

| | |
|---|---|
| Methyl salycylate | 0.0350 g |
| Pharmasol T-115 ® (Nissan Chemical Industries, Ltd.) | 2.0000 g |
| α-carotene | 0.0100 g |

What is claimed is:

1. A method of inhibiting the growth of cancer cells which are susceptible to treatment with α-carotene, said method consisting essentially of:
    administerting an effective cancer cell growth inhibiting amount of α-carotene to a mammal having said cancer cells.
2. The method of claim 1, wherein said mammal is a human.
3. The method of claim 2, wherein said cancer which is susceptible to treatment with α-carotene is a cancer of ectodermal origin.

4. The method of claim 2, wherein said cancer which is susceptible to treatment with α-carotene is a cancer of endodermal origin.

5. The method of claim 2, wherein purified α-carotene is administered to said human.

6. The method of claim 2, wherein said α-carotene is administered orally.

7. The method of claim 2, wherein said α-carotene is administered by injection.

8. The method of claim 1, wherein said cancer cells which are inhibited are selected from the following:
pancreatic cancer cells;
gastric cancer cells;
hepatic cancer cells;
glioblastoma cells;
neuroblastoma cells;
leukemia cancer cells; or
cervic cancer cells.

9. The method of claim 2, wherein said cancer cells which are inhibited are selected from the following:
pancreatic cancer cells;
gastric cancer cells;
hepatic cancer cells;
glioblastoma cells;
neuroblastoma cells;
leukemia cancer cells; or
cervic cancer cells.

* * * * *